(12) United States Patent
Salvat, Jr.

(10) Patent No.: US 7,868,754 B2
(45) Date of Patent: Jan. 11, 2011

(54) MEDICAL SYSTEM AND TRACKING DEVICE

(75) Inventor: Roberto Salvat, Jr., Suwanee, GA (US)

(73) Assignee: S.I.P. Holdings, LLC, Palm Beach Gardens, FL (US)

( * ) Notice: Subject to any disclaimer, the term of this patent is extended or adjusted under 35 U.S.C. 154(b) by 328 days.

(21) Appl. No.: 11/861,858

(22) Filed: Sep. 26, 2007

(65) Prior Publication Data

US 2009/0079569 A1   Mar. 26, 2009

(51) Int. Cl.
G08B 1/08 (2006.01)
G08B 13/14 (2006.01)

(52) U.S. Cl. .............. 340/539.13; 340/539.12; 340/572.1

(58) Field of Classification Search ........... 340/539.13, 340/539.12, 571, 572.1
See application file for complete search history.

(56) References Cited

U.S. PATENT DOCUMENTS

| | | | |
|---|---|---|---|
| 6,490,351 B1 | 12/2002 | Roberts | |
| 6,828,908 B2 | 12/2004 | Clark | |
| 7,091,266 B2 | 8/2006 | Murakami et al. | |
| 7,102,508 B2 | 9/2006 | Edelstein et al. | |
| 7,138,902 B2 | 11/2006 | Menard | |
| 7,158,030 B2 * | 1/2007 | Chung | 340/572.1 |
| 7,158,754 B2 | 1/2007 | Anderson | |
| 7,171,187 B2 | 1/2007 | Haave et al. | |
| 7,268,684 B2 * | 9/2007 | Tethrake et al. | 340/572.1 |
| 7,420,468 B2 * | 9/2008 | Fabian et al. | 340/572.1 |
| 7,557,710 B2 * | 7/2009 | Sanchez et al. | 340/572.1 |
| 7,728,729 B2 * | 6/2010 | Christopher | 340/572.1 |
| 2002/0067263 A1 * | 6/2002 | Tafoya et al. | 340/572.1 |
| 2003/0091612 A1 | 5/2003 | Sabesan | |
| 2005/0183990 A1 | 8/2005 | Corbett, Jr. | |
| 2006/0017545 A1 | 1/2006 | Volpi et al. | |
| 2006/0043179 A1 | 3/2006 | Nycz et al. | |
| 2006/0093744 A9 | 5/2006 | Suzuki et al. | |
| 2006/0109105 A1 * | 5/2006 | Varner et al. | 340/539.12 |
| 2006/0145871 A1 | 7/2006 | Donati et al. | |
| 2007/0001809 A1 | 1/2007 | Kodukula et al. | |
| 2007/0028642 A1 | 2/2007 | Glade et al. | |
| 2007/0160494 A1 | 7/2007 | Sands | |
| 2007/0222122 A1 | 9/2007 | Oug et al. | |
| 2008/0030345 A1 | 2/2008 | Austin et al. | |
| 2008/0150722 A1 | 6/2008 | Jackson | |

* cited by examiner

*Primary Examiner*—Jennifer Mehmood
(74) *Attorney, Agent, or Firm*—McHale & Slavin, P.A.

(57) ABSTRACT

A tracking device and system for tracking medical supplies, in particular, medical trays and their components is disclosed. The tracking device utilizes GPRS/GSM technology to enable an individual to locate and monitor the movement of a medical tray at any given time and for any desired period of time. The tracking system utilizes geo-fences established within buildings to assist in determining the specific location of the medical trays within these buildings. The tracking devices can also be activated by motion sensors to alert the tracking system of a possible theft of the tray. The tracking system incorporates software which enables an individual to determine the location of medical trays, determine the contents of the trays and schedule the use of the medical trays by specific doctors and at specific locations. The tracking system also retains information regarding the doctors, the medical device manufacture representatives, the hospitals and sales of the medical devices.

59 Claims, 24 Drawing Sheets

TRAY AVAILABILITY
TOTAL RECORDS: 124

| TRAY NUMBER | TRAY TYPE | CURRENTLY AT | DATE DUE | DATE AVAILABLE AFTER USE | NEED FOR SURGERY AT | SURGERY DATE | TRAY ID |
|---|---|---|---|---|---|---|---|
| 1112223 | ANTERIOR GENERAL INSTRUMENT TRAY | GWINNETT MEDICAL | 8/15/2007 | 8/17/2007 | NORTHSIDE HOSPITAL | 8/17/2007 | 20 |
| 1112223 | ANTERIOR GENERAL INSTRUMENT TRAY | GWINNETT MEDICAL | 8/3/2007 | 8/5/2007 | ST JOSEPHS OF ATLANTA | 8/15/2007 | 20 |
| 1112223 | ANTERIOR GENERAL INSTRUMENT TRAY | GWINNETT MEDICAL | 9/18/2007 | 9/20/2007 | NORTH HOSPITAL | 9/20/2007 | 20 |
| 11235 | ANTERIOR GENERAL INSTRUMENT TRAY | GRADY HOSPITAL | 8/8/2007 | 8/10/2007 | GRADY HOSPITAL | 8/10/2007 | 21 |
| 11235 | ANTERIOR GENERAL INSTRUMENT TRAY | GRADY HOSPITAL | 8/11/2007 | 8/13/2007 | GRADY HOSPITAL | 8/17/2007 | 21 |
| 11235 | ANTERIOR GENERAL INSTRUMENT TRAY | GRADY HOSPITAL | 8/29/2007 | 8/31/2007 | GRADY HOSPITAL | 8/31/2007 | 21 |
| 11235 | ANTERIOR GENERAL INSTRUMENT TRAY | GRADY HOSPITAL | 8/11/2007 | 8/13/2007 | GRADY HOSPITAL | 8/20/2007 | 21 |
| 11235 | ANTERIOR GENERAL INSTRUMENT TRAY | GRADY HOSPITAL | 8/13/2007 | 8/15/2007 | GRADY HOSPITAL | 8/15/2007 | 21 |
| 11235 | ANTERIOR GENERAL INSTRUMENT TRAY | GRADY HOSPITAL | 8/24/2007 | 8/26/2007 | GRADY HOSPITAL | 8/26/2007 | 21 |
| 11235 | ANTERIOR GENERAL INSTRUMENT TRAY | GRADY HOSPITAL | 8/29/2007 | 8/31/2007 | GRADY HOSPITAL | 8/31/2007 | 21 |
| 99887745 | CERVICAL ALLOGRAFT TRAY | GRADY HOSPITAL | 8/8/2007 | 8/10/2007 | GWINNETT MEDICAL | 8/9/2007 | 17 |
| 99887745 | CERVICAL ALLOGRAFT TRAY | GRADY HOSPITAL | 9/2/2007 | 9/4/2007 | NORTH FULTON HOSPITAL | 9/4/2007 | 17 |
| 99887745 | CERVICAL ALLOGRAFT TRAY | GRADY HOSPITAL | 9/4/2007 | 9/6/2007 | NORTH FULTON HOSPITAL | 9/6/2007 | 17 |
| 99887745 | CERVICAL ALLOGRAFT TRAY | GRADY HOSPITAL | 9/9/2007 | 9/11/2007 | NORTH FULTON HOSPITAL | 9/11/2007 | 17 |
| 99887745 | CERVICAL ALLOGRAFT TRAY | GRADY HOSPITAL | 7/31/2007 | 8/2/2007 | GRADY HOSPITAL | 8/2/2007 | 17 |
| 99887746 | CERVICAL ALLOGRAFT TRAY | SCOTTISH HOSPITAL | 8/26/2007 | 8/28/2007 | NORTH FULTON HOSPITAL | 8/28/2007 | 18 |
| 99887746 | CERVICAL ALLOGRAFT TRAY | SCOTTISH HOSPITAL | 8/28/2007 | 8/30/2007 | NORTH FULTON HOSPITAL | 8/28/2007 | 18 |
| 99887746 | CERVICAL ALLOGRAFT TRAY | SCOTTISH HOSPITAL | 8/27/2007 | 8/29/2007 | NORTH FULTON HOSPITAL | 8/29/2007 | 18 |

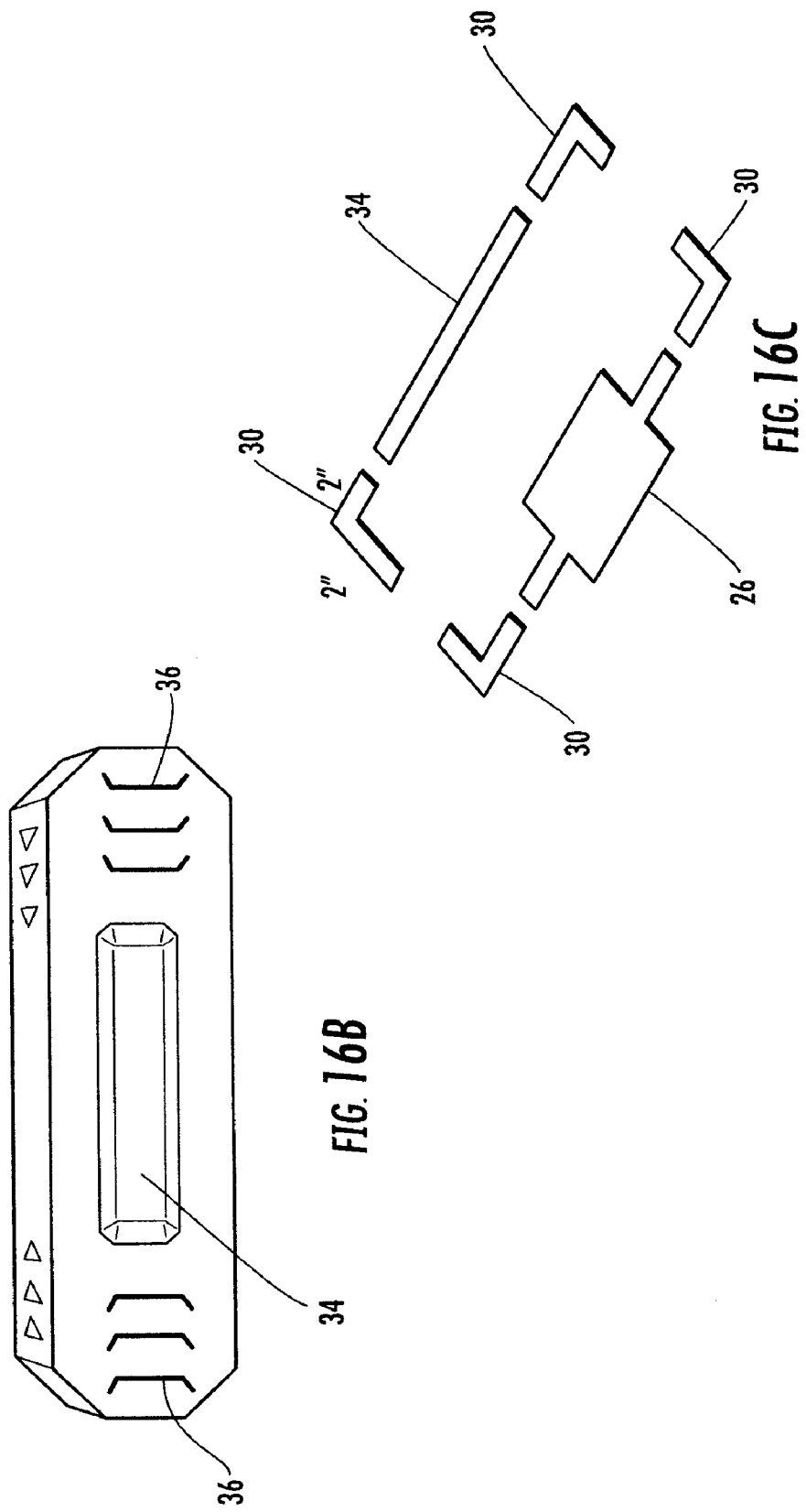

MEDICAL SYSTEM AND TRACKING DEVICE

FIELD OF THE INVENTION

The present invention relates to medical supplies and in particular to an apparatus and system for tracking and locating these medical supplies.

BACKGROUND OF THE INVENTION

Recent advances in medical technology and procedures have yielded a number of devices including spinal implants; hip, knee, shoulder and other orthopedic replacements; pacemakers and other implantable devices. These devices are very costly and normally require the presence of a manufacture's representative to assist the surgeon in utilizing the device properly. These devices are shipped from the manufacture to the hospital in surgical trays. These surgical trays include the medical device and any other equipment required during the medical procedure to install or implant the device. The cost of these medical devices and related equipment is very high, usually exceeding tens of thousands of dollars. This has resulted in a black market for these medical devices.

These surgical trays, including the medical devices, must be available when the surgeon is scheduled to perform the operation. In many instances, like hip and knee replacement, the medical devices are specifically sized for the individual patient. Therefore, an inventory of these devices cannot be maintained in the hospital. If the specific surgical tray required for a surgery cannot be located, the surgery must be postponed. This results in unnecessary costs on behalf of the surgeon and hospital. In addition, these surgical trays, including all of their components, must be sterilized prior to their use.

Another problem is theft of the trays between the manufacturing facility and the operating room. Once the surgical tray is delivered to the hospital and someone accepts shipment, the surgical tray becomes the property and responsibility of the hospital. There have also been instances of theft within the hospitals. In some instances the trays have been shipped to the incorrect hospital and this has not been discovered until the day of the surgery. This shipping error will again result in postponement of the surgery and related expenses.

Therefore, what is needed in the art is a tracking device and system for tracking these surgical trays and other medical supplies from the manufacturer to the operating room. This would enable the medical device manufacture's field representative to locate and monitor the surgical tray containing the medical device from the time is left the manufacturing facility until it arrived in the operating room. The system is also capable of ordering additional supplies and billing for the use of the medical supplies and equipment.

DESCRIPTION OF THE PRIOR ART

U.S. Published Patent Application No. 2006/0017545 discloses a tracking system for monitoring the location of an object or a group of objects using RFID tags. These tags must be passed by an interrogator or tracking device to be detected. If the RFID devices are not within the range of the tracking devices, such an in a hospital store room, the tracking devices are unable to located the RFID devices. Some of these RFID tags can include a GPS feature to report their location. However, if the tags cannot communicate with the GPS satellites, such as when they are located within buildings, their location cannot be determined. Therefore, this system is not practical when tracking medical trays in hospitals.

U.S. Pat. No. 7,158,754, issued to Anderson and U.S. Pat. No. 7,158,030, issued to Chang, both disclose RFID tags which can be encapsulated on or attached to medical devices. These tags can only be tracked when they are passed by an interrogator or other tracking device. They cannot be located by tracking devices positioned outside of the building when they are within the building.

SUMMARY OF THE INVENTION

Briefly, the present invention is directed toward a tracking device and system for tracking medical supplies, in particular, medical trays and their components. The tracking device utilizes GPRS/GSM technology to enable an individual to locate and monitor the movement of a surgical tray at any given time and for any desired period of time. The tracking system utilizes geo-fences established within buildings to assist in determining the specific location of the surgical trays within these buildings. Whenever a surgical tray passes one of these geo-fences the tracking device is activated and a signal is sent to an individual or device monitoring the location of the surgical tray. The tracking devices can also be activated by motion sensors to alert the tracking system of a possible theft of the surgical tray. The tracking system can also be programmed so the tracking device transmits its position at specific time intervals. The tracking device can also utilize other wireless communications such as Bluetooth or Wi-Fi.

The tracking device is normally attached to a surgical tray in a manner such that only the individual who installed the tracking device or company providing the tracking service can remove the tracking device. This prevents the tracking device from being removed from the surgical tray and left at a known location, such as the store room of a hospital, while the surgical tray is stolen. Normally the only time the tracking device needs to be removed from the surgical tray is to replace the batteries. The tracking device can also be equipped with a pager or beeper to assist in determining its location in large store rooms.

The tracking device is also weather/water proof and capable of withstanding elevated temperatures, such as those encountered in an autoclaving process. The tracking device includes a shock and heat absorption insulation system to protect the device.

Accordingly, it is an objective of the instant invention to provide a system for tracking a medical device tray and its contents at all locations including inside of buildings.

It is a further objective of the instant invention to provide a tracking device which can withstand the medical instruments sterilization environments.

It is yet another objective of the instant invention to provide a system for tracking medical devices which includes information regarding the intended user of the devices, the location at which the devices are to be used and the representative of the device manufacturer.

It is a still further objective of the invention to enable the medical devices to be ordered and shipped to the desired locations when required.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 6 is a web page for entering hospital data;

FIG. 10 is a web page illustrating a schedule of surgeries;

FIG. 12 is a web page illustrating medical tray availability;

DETAILED DESCRIPTION OF THE INVENTION

Figure 1A:
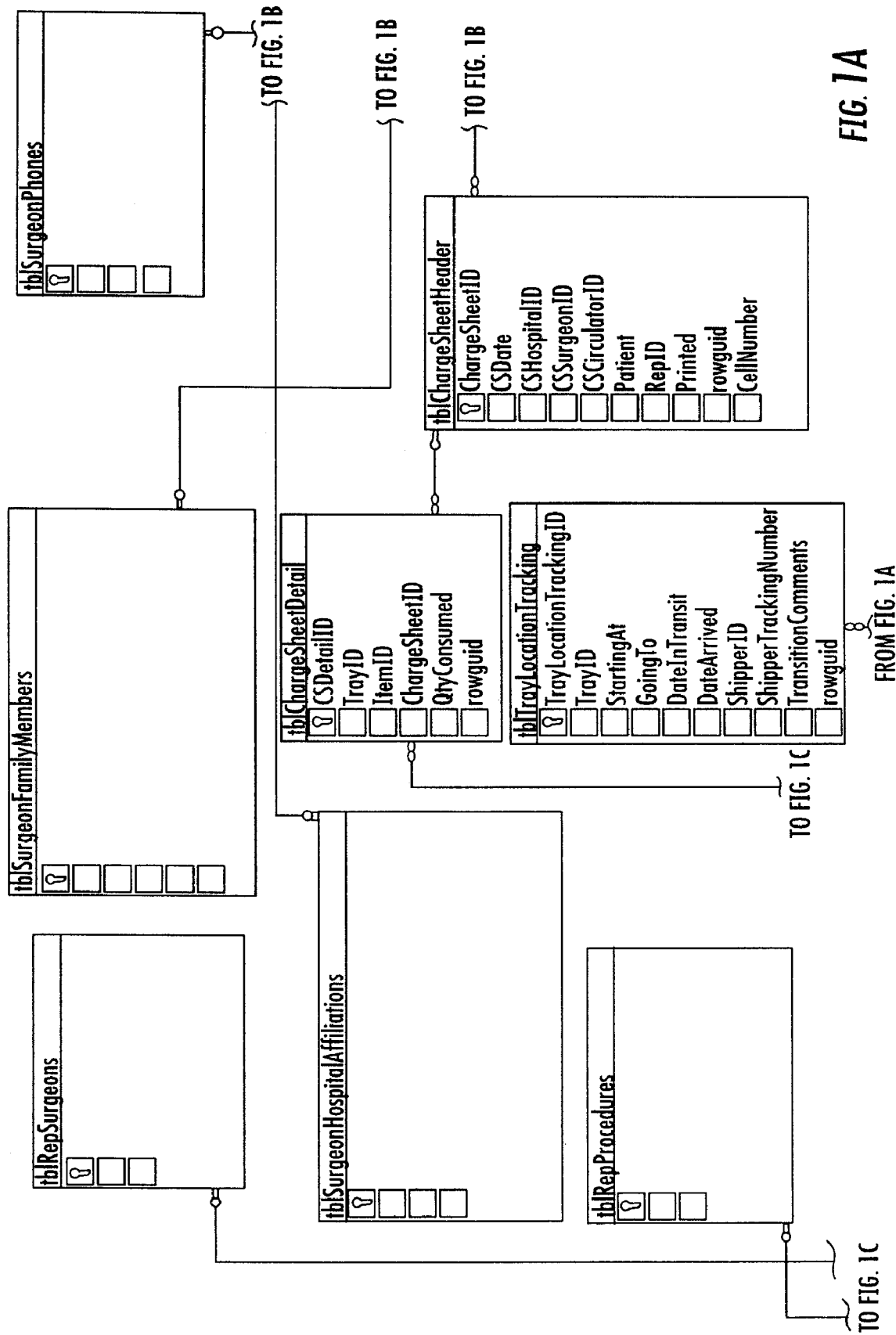
FIGS. 1 A-D are an overall flowchart of the various aspects of the data base and haw they are connected.
Figure 1B:
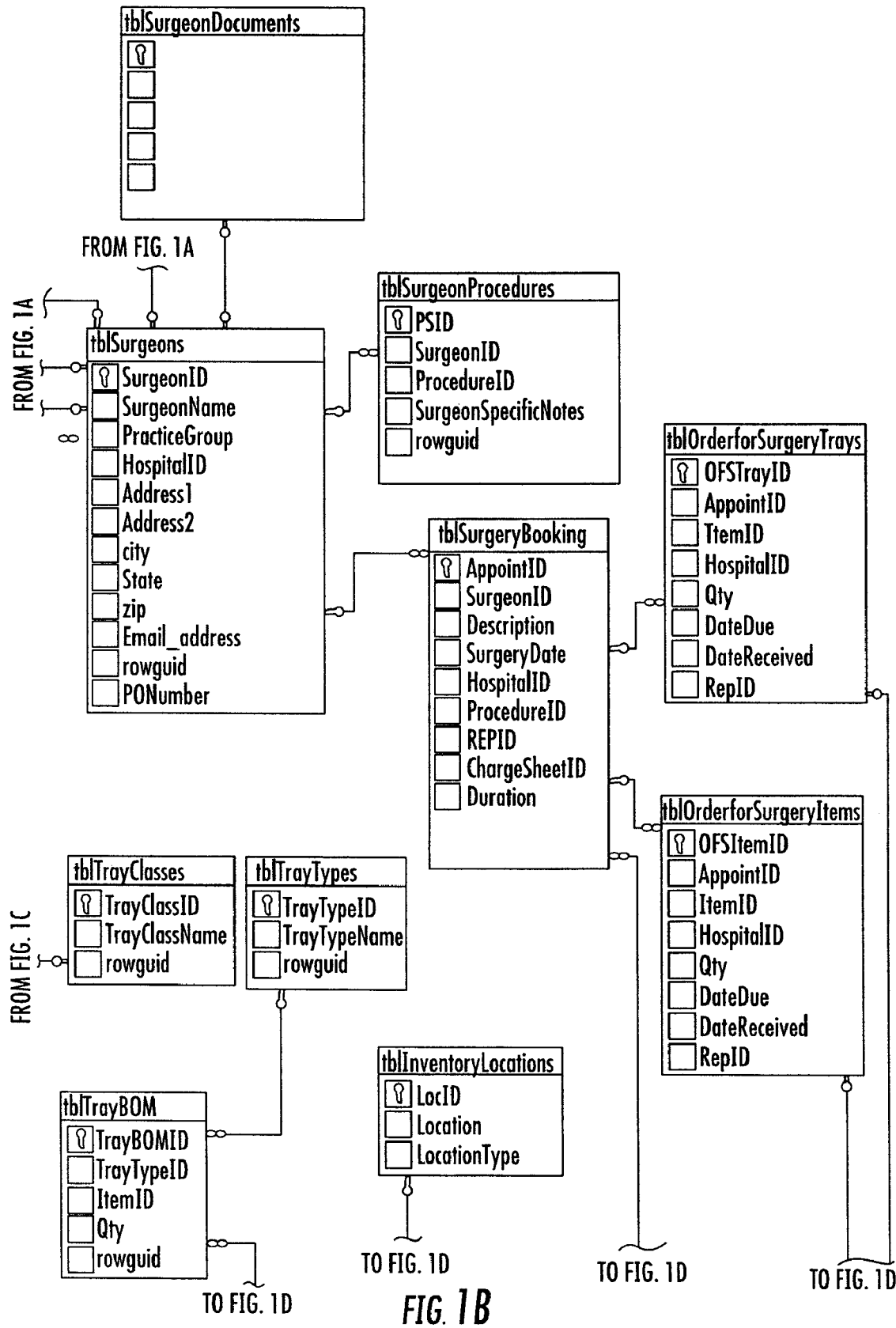
Figure 1C:
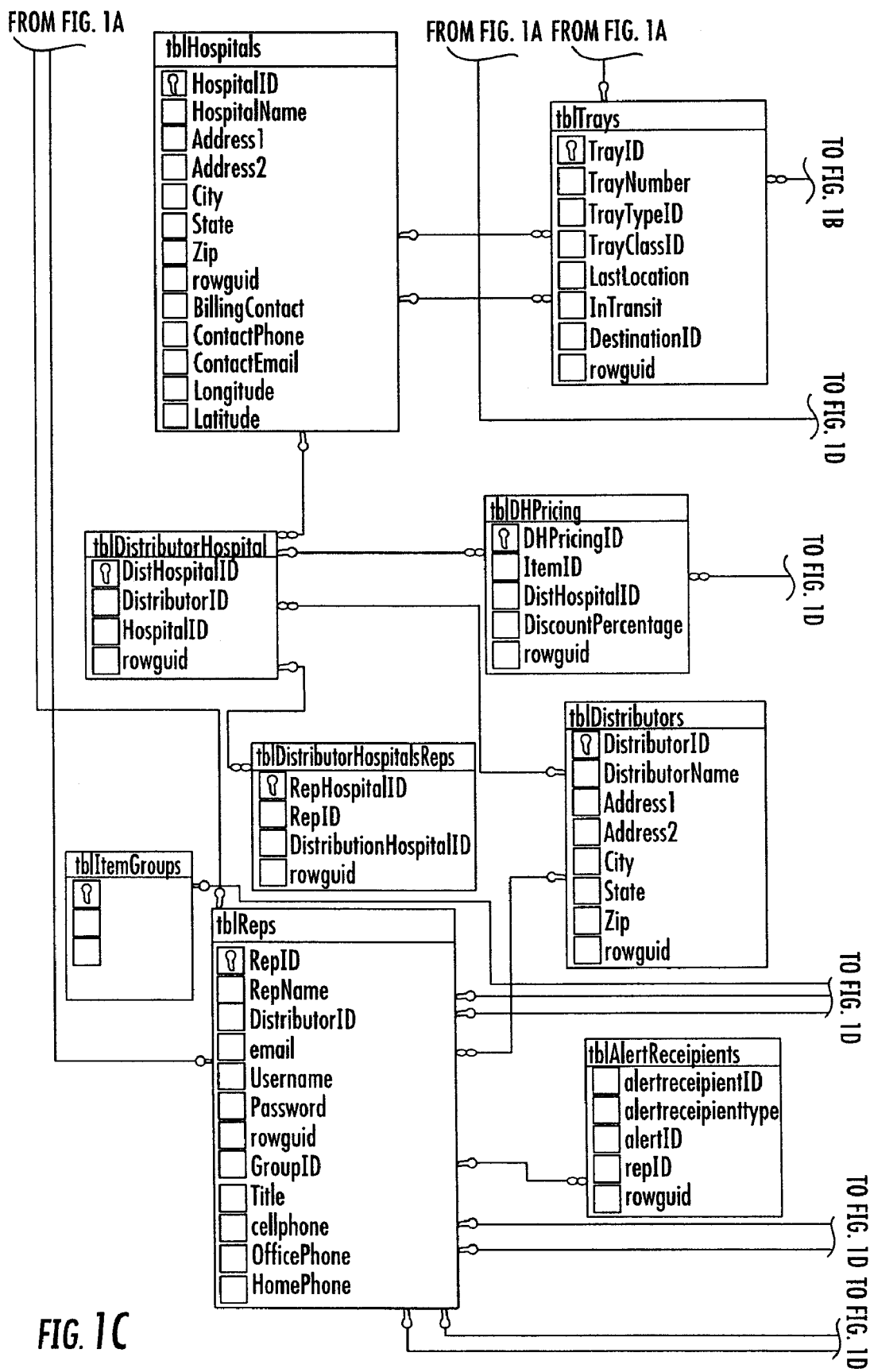
Figure 1D:
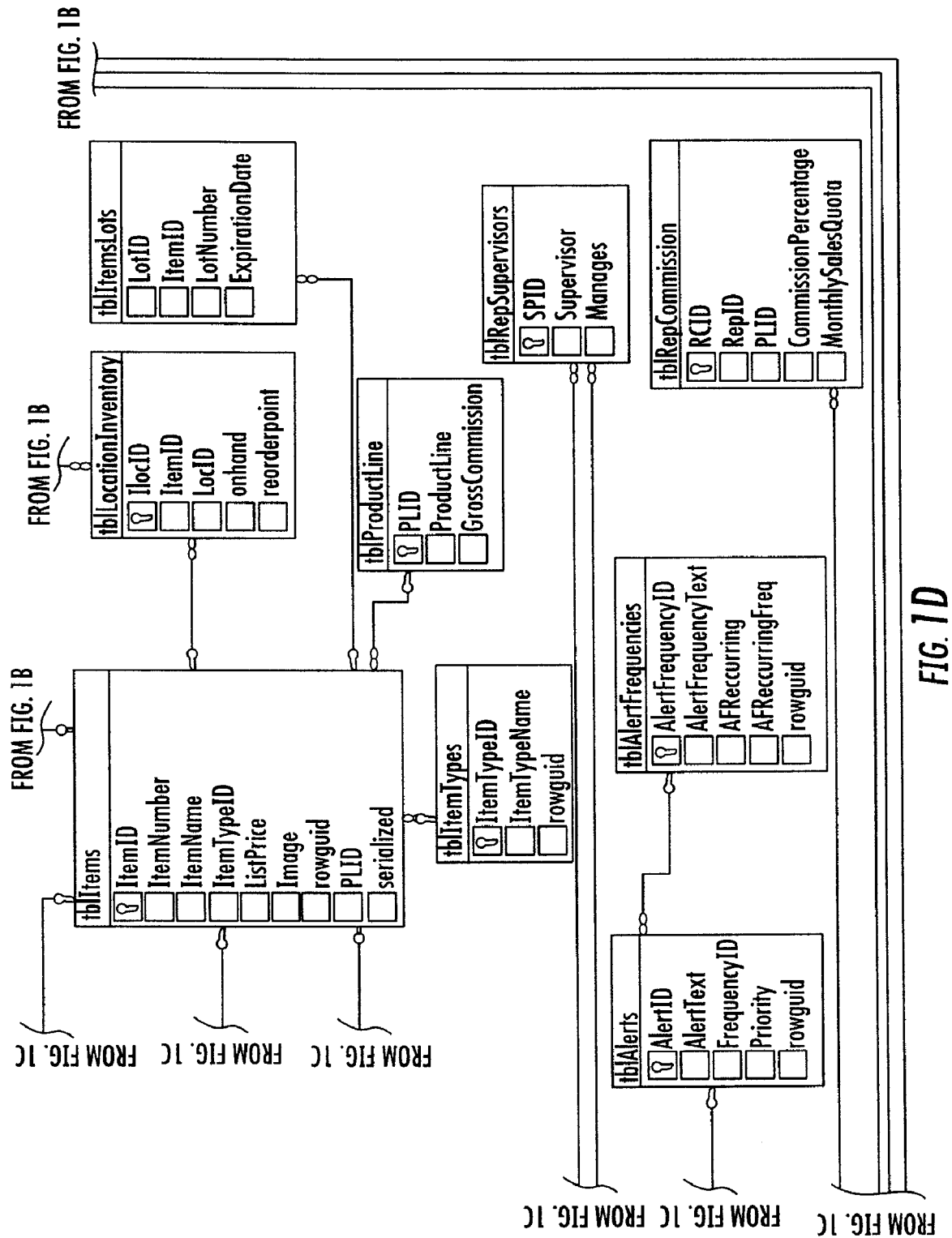
Figure 2A:
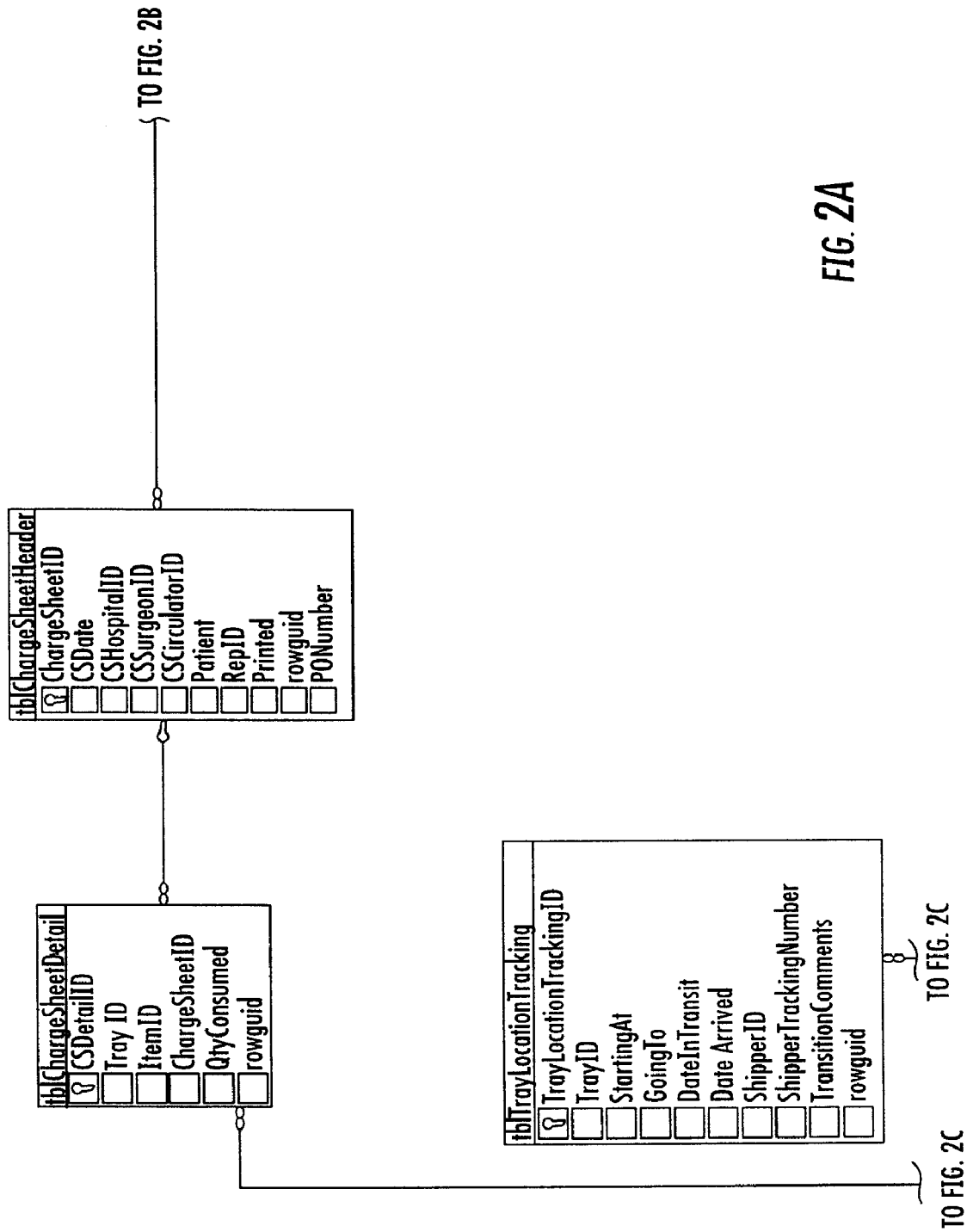
FIGS. 2 A-D are a flowchart similar to FIGS. 1 A-D with some additional information.
Figure 2B:
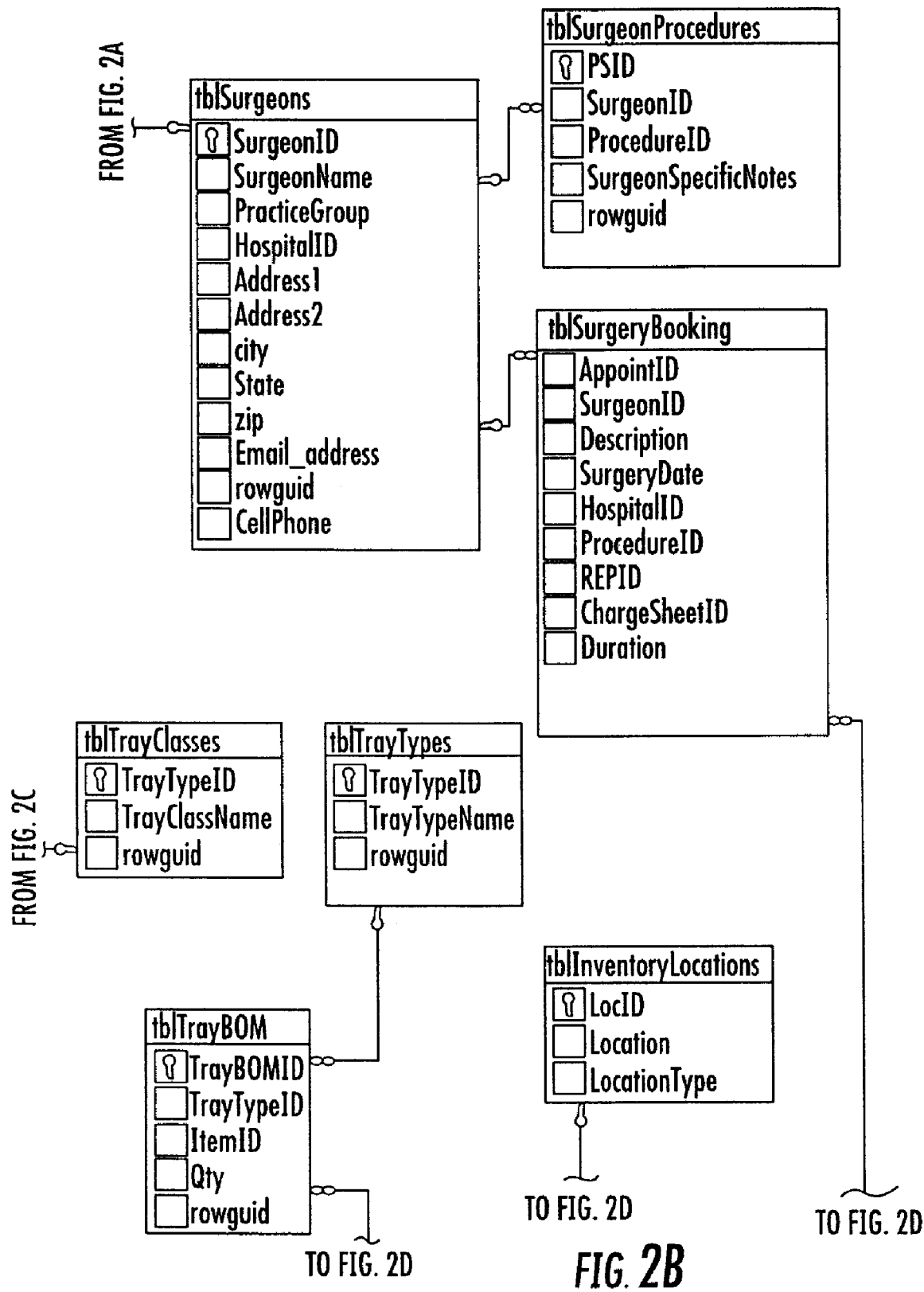
Figure 2C:
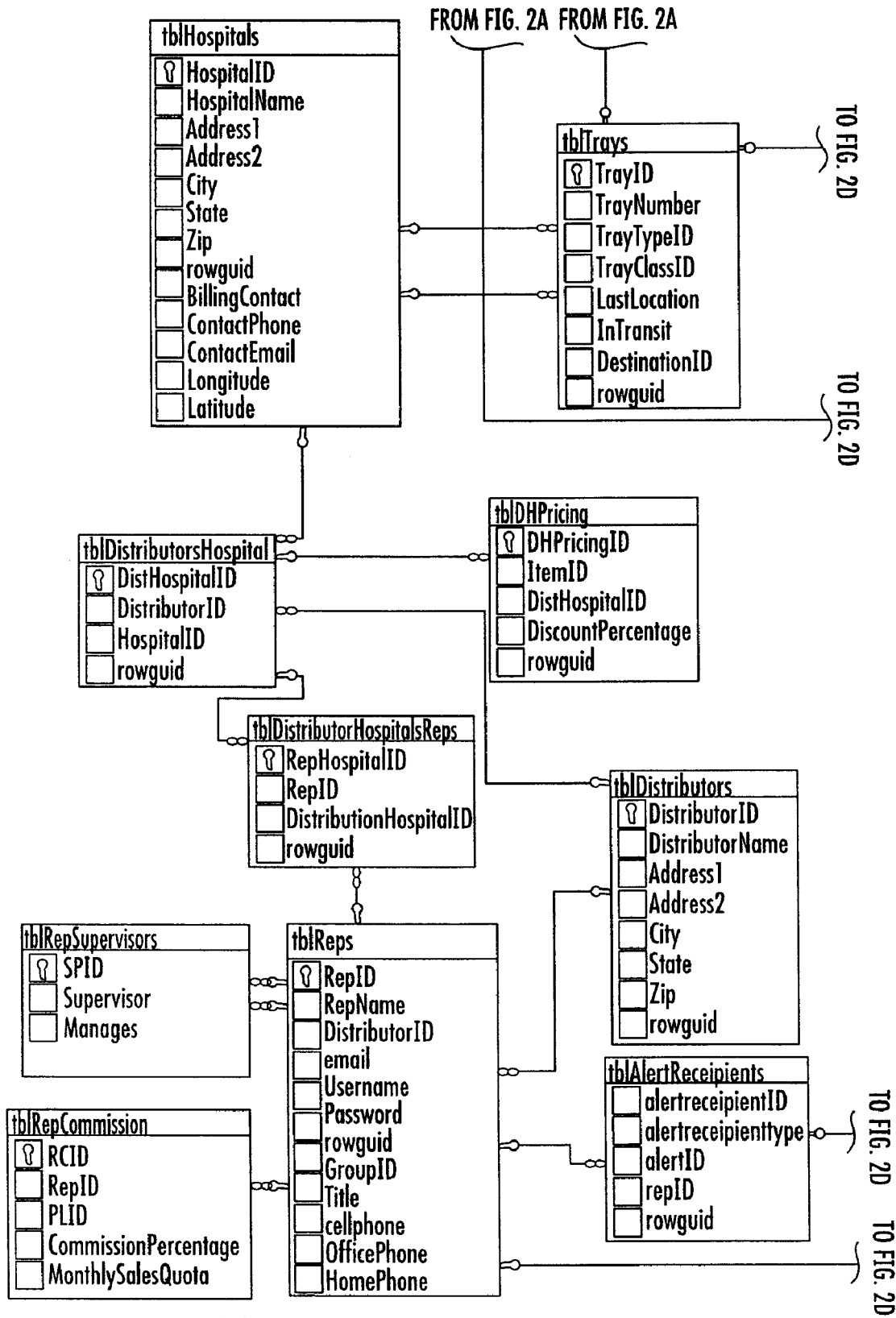
Figure 2D:
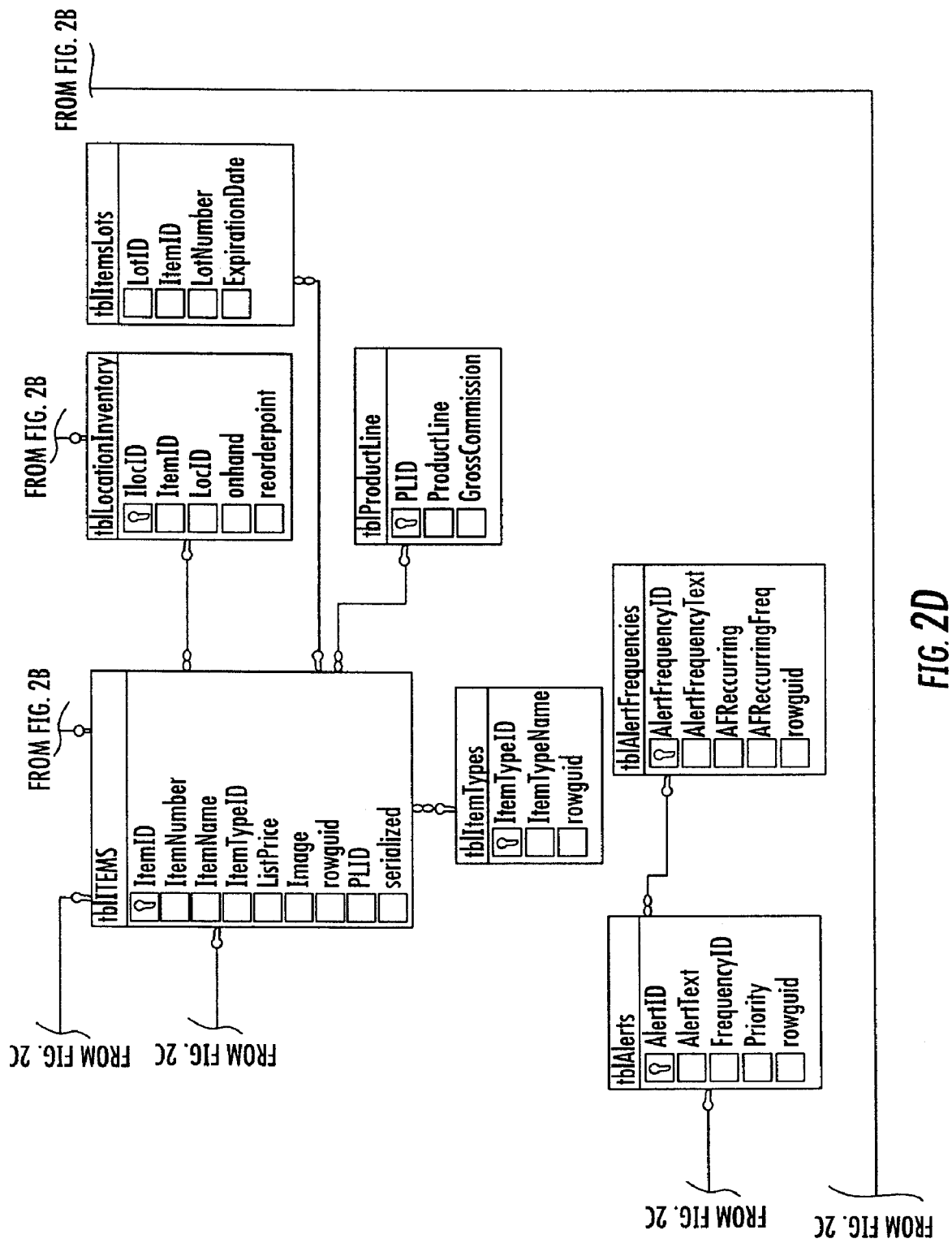

While the present invention is susceptible of embodiment in various forms, there is shown in the drawings and will hereinafter be described a presently preferred, albeit non limiting, embodiment with the understanding that the present disclosure is to be considered an exemplification of the present invention and is not intended to limit the invention to the specific embodiments illustrated.

A system and method for tracking an object, an article or an individual as it moves along a path is disclosed hereinafter. The system and method of the present invention do not require input from an individual whenever the object or article moves from one location to another. A position indication device such as a RFID (Radio Frequency Identification) and/or GPS (Global Positioning System) device is attached directly to or located in close proximity to the article or object which is being tracked. Various types of GPS systems which are available for use include National Differential GPS System (NDGPS); Wide Area Augmentation System (WAAS); Continuously Operating Reference Station (CORS); Global Differential GPS (GDGPS) and International GNSS Service (IGS). Other types of position indicating devices may be used in place of the RFID or GPS devices. The positioning indicating device will transmit its location utilizing GPS (Global Positioning System); GSM (Global System for Mobile communications); CDMA (Code Division Multiple Access); or SMS (Short Message Service) technologies or a combination thereof.

The system is accessed through a web site wherein medical device reps, surgeons, hospital personnel and surgical device manufactures can access information relating to the medical trays and their location. The trays can be ordered and transferred utilizing this web site. The costs of the trays can also be billed at this web site.

FIG. 1 illustrates how the various menus are linked to each other so that the medical device reps can access all the information pertaining to the trays and the surgical procedures in which they are to be used. The various menus illustrated in FIG. 1 include, the Rep Surgeons, the Surgeon Family Members, the Surgeon Phones, the Surgeon Documents, the Surgeon Hospital Affiliations, the Charge Detail Sheet, the Charge Sheet Header, the Surgeons, the Surgeon Procedures, the Order for Surgery Trays, the Rep Procedures, the Tray Location Tracking, the Surgery Booking, the Hospitals, the Trays, the Tray Classes, the Tray Types, the Inventory Locations, the Order for Surgery Items, the Tray BOM, the Distributor or Hospital, the DH Pricing, the Items, the Location Inventory, the Item Lots, the Product Line, the Distributor Hospitals Reps, the Distributors, the Item Types, the Item Groups, the Reps, the Alert Recipients, the Alerts, the Alert Frequencies, the Rep Supervisors and the Rep Commission.

FIG. 2 also illustrates how various menus are linked to each other so that the medical device reps can access all the information pertaining to the trays and the surgical procedures in which they are to be used. The various menus illustrated in FIG. 2 include the Charge Sheet Detail, the Charge Sheet Header, the Surgeons, the Surgeon Procedures, the Surgery Booking, the Tray Location Tracking, the Hospitals, the Trays, the Tray Classes, the Tray Types, the Inventory Locations, the Tray BOM, the Distributor Hospital, the DH Pricing, the Items, the Location Inventory, the Item Lots, the Product Line, the Distributor Hospital Reps, the Distributors, the Item Types, the Rep Supervisors, the Reps, the Alert Recipients, the Alerts, the Alert Frequencies and the Rep Commission.

Figure 3:
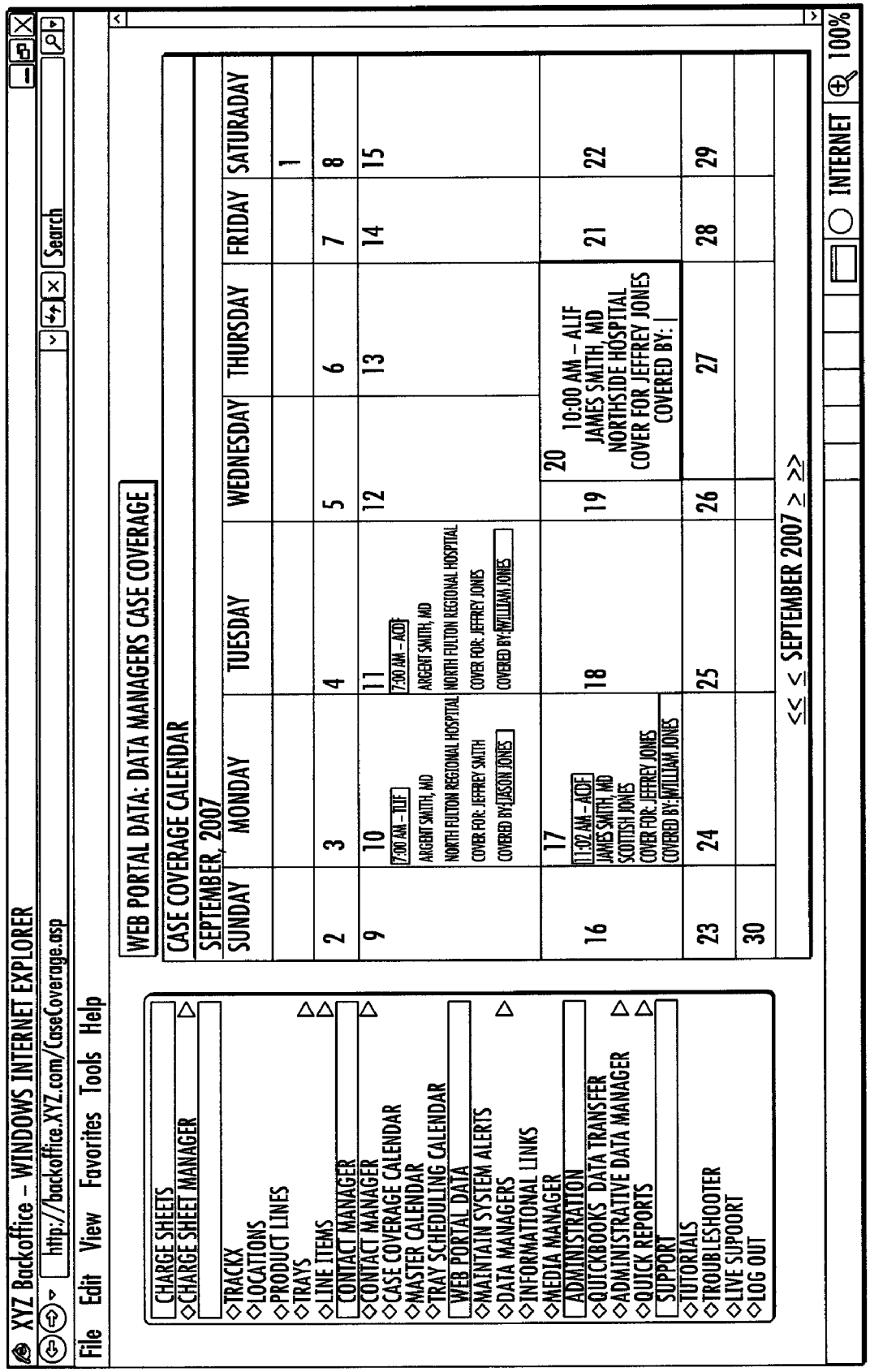
FIG. 3 is a web page of the system illustrating the scheduling of surgeries.

An example of the case coverage for different surgical procedures is illustrated in FIG. 3. For example on Monday, Sep. 10, 2007 the time and type of the procedure is listed at the top, 7:00 AM-TLIF. Next the name of the surgeon is listed, Argent Agrawal. Next the hospital where the procedure is being done is listed, North Fulton Regional Hospital. Next the name of the medial device rep. present at the procedure is listed, Jeffery Smith. Finally if the rep. is not available his replacement is listed, Jason Graves. The charge sheet menu appears in all of the web pages. This enables the user to quickly access the information that he or she is seeking.

Figure 4:
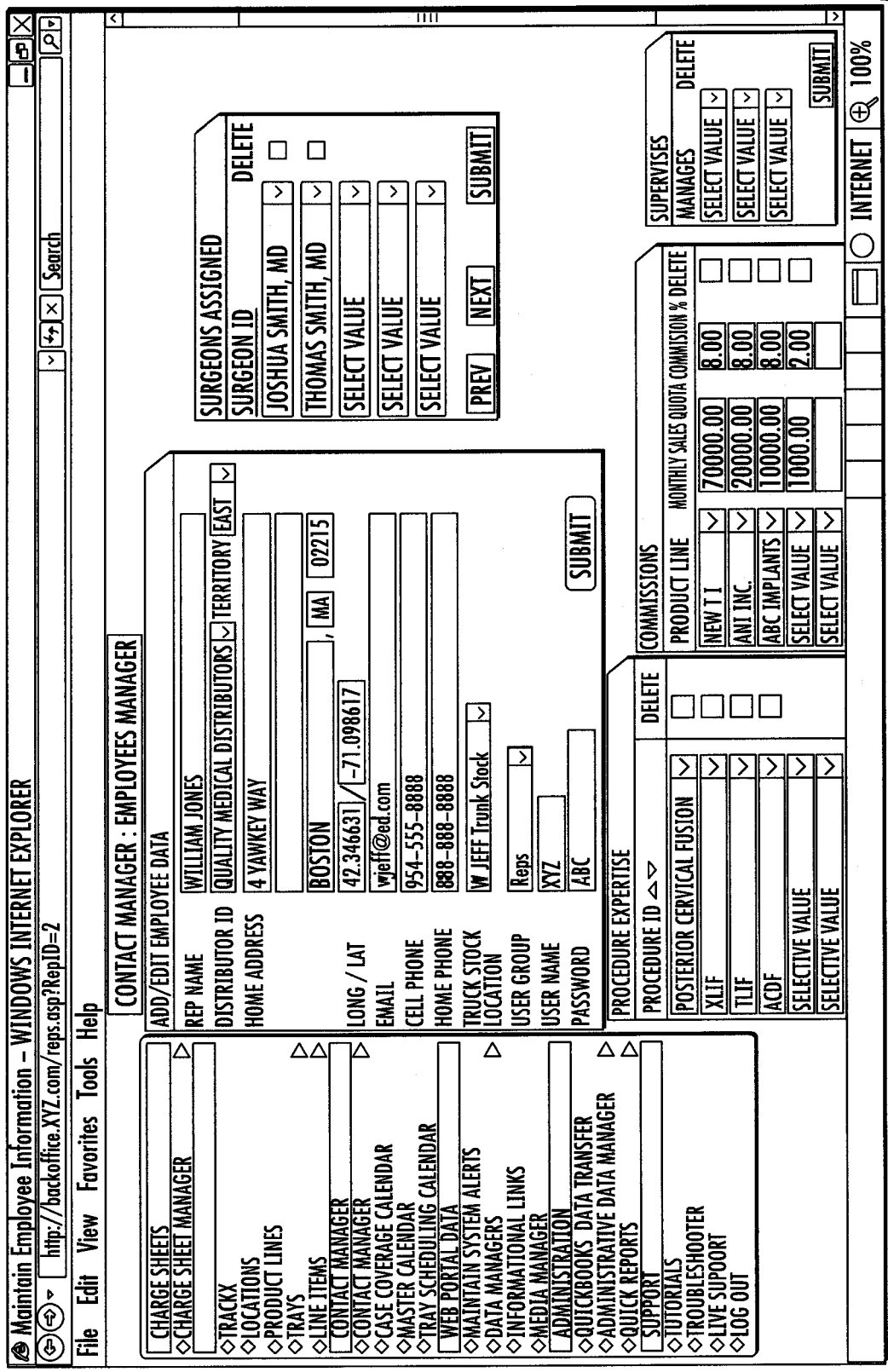
FIG. 4 is a web page of the system illustrating how data is entered regarding medical devices representatives.

An example of the information with respect to each surgical rep. is illustrated in FIG. 4. The reps. personal information is available including how he can be contacted. The surgeons he is assigned to are also illustrated. The surgical procedures in which he has an expertise are listed. His commissions for the use of various medical devices are listed. Finally, all personal that he supervises are also listed.

Figure 5:
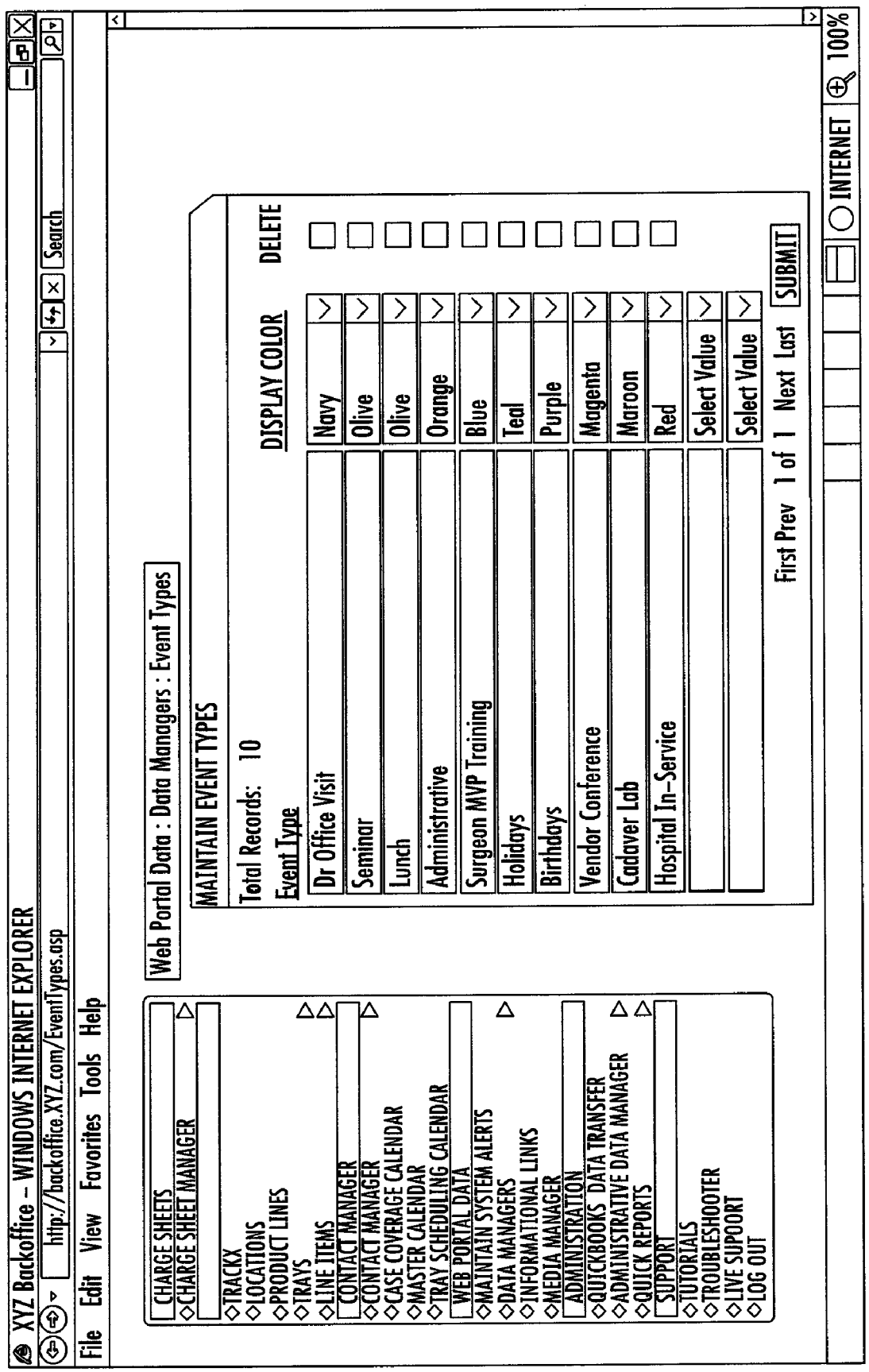
FIG. 5 is a web page illustrating the color codes on the charge sheet.
Figure 6:
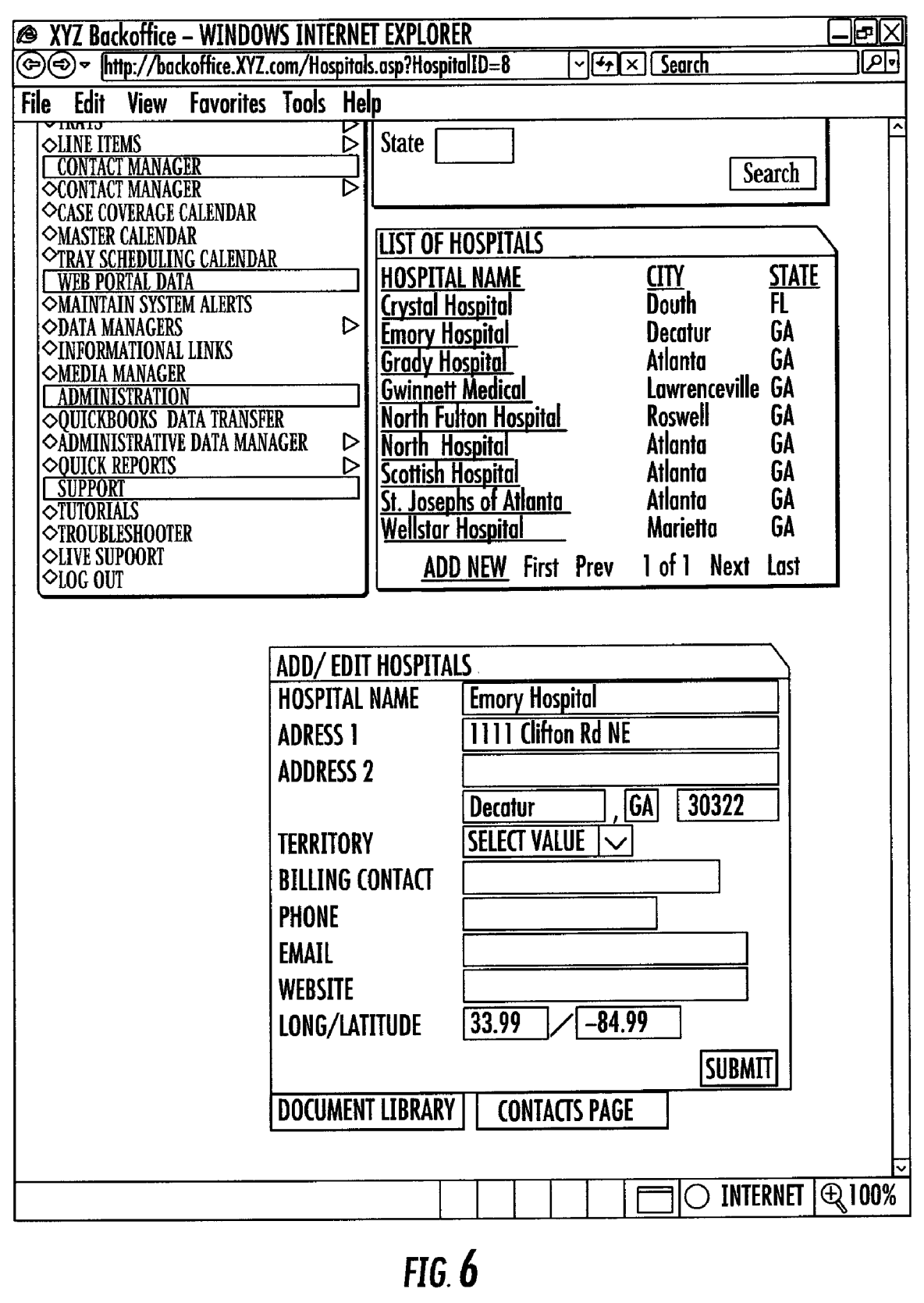
Figure 7:
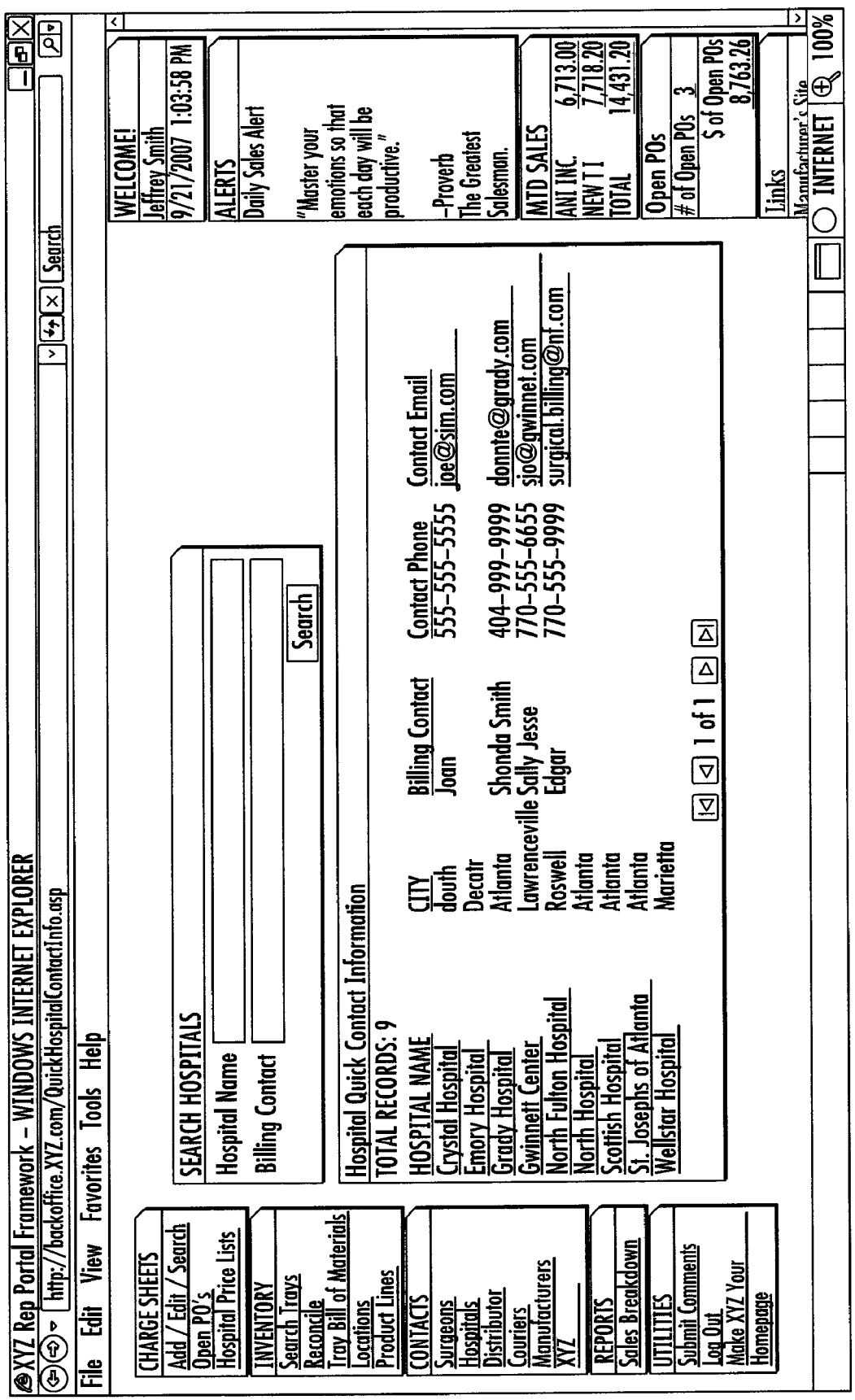
FIG. 7 is a web page for obtaining hospital data.

FIG. 5 is a menu of the various colors which are assigned to various events. For example, doctor visits are navy, Surgeon training is blue and hospital in-service is red. These colors are utilized in the case coverage illustrated in FIG. 3. Hospital information is illustrated in FIG. 6. A list of the hospitals which utilize the medical trays is provided. When a particular hospital is selected the address and location of the hospital is provided. Also information regarding billing is provided. Another method of accessing hospital information is illustrated in FIG. 7. The hospital or billing contact can be searched in the system. This web page also includes a quick contact information list.

Figure 8:
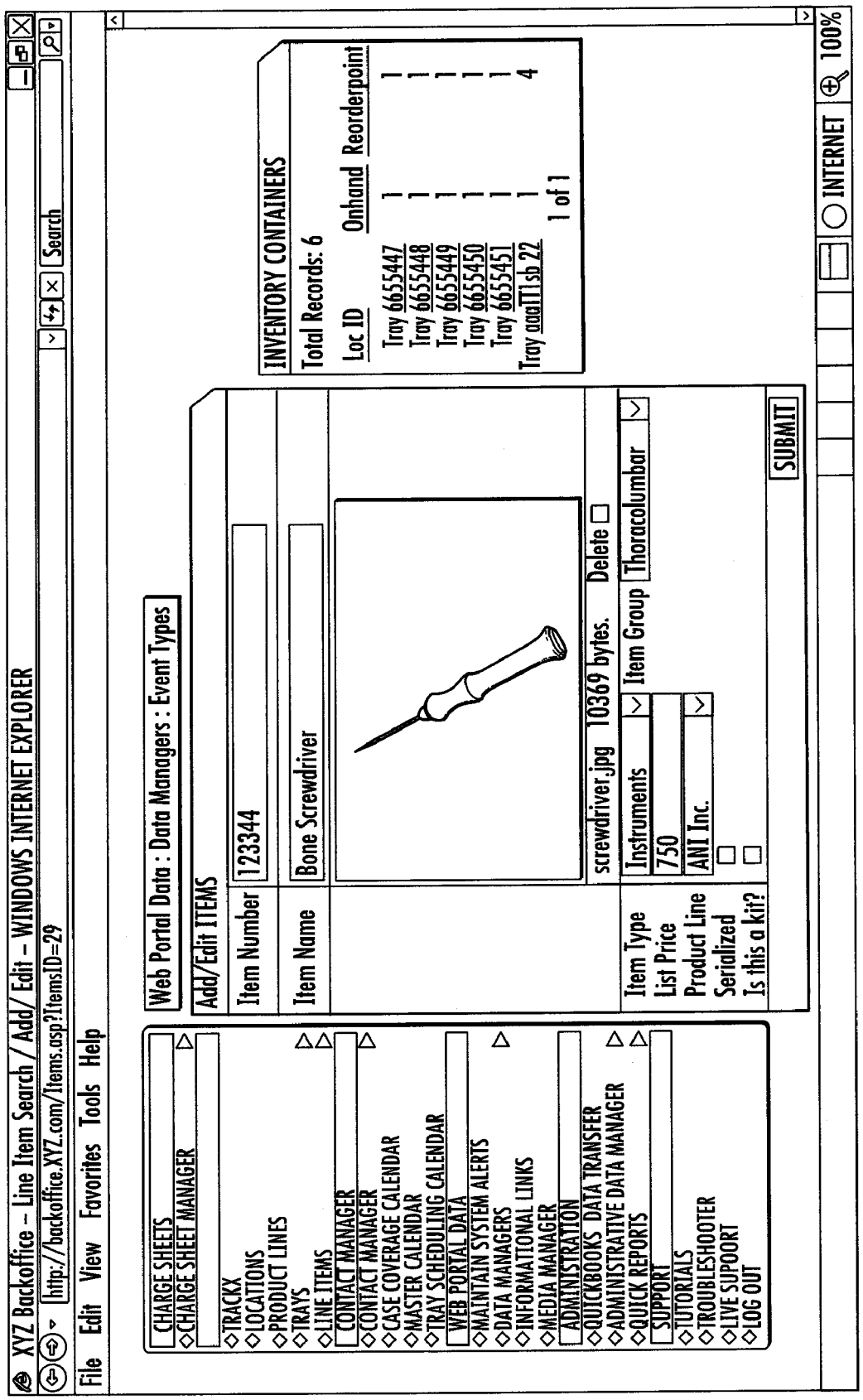
FIG. 8 is a web page illustrating medical device information.

The contents of the various medical trays is illustrated in the web page in FIG. 8. A description of each of the items including a photograph, the procedure in which they are used, the cost of the items and the manufacturer are readily available. An inventory of the various trays is also available. Utilizing this information the surgical rep. can familiarize himself or herself with the contents of each tray prior to the surgical procedure.

Figure 9:
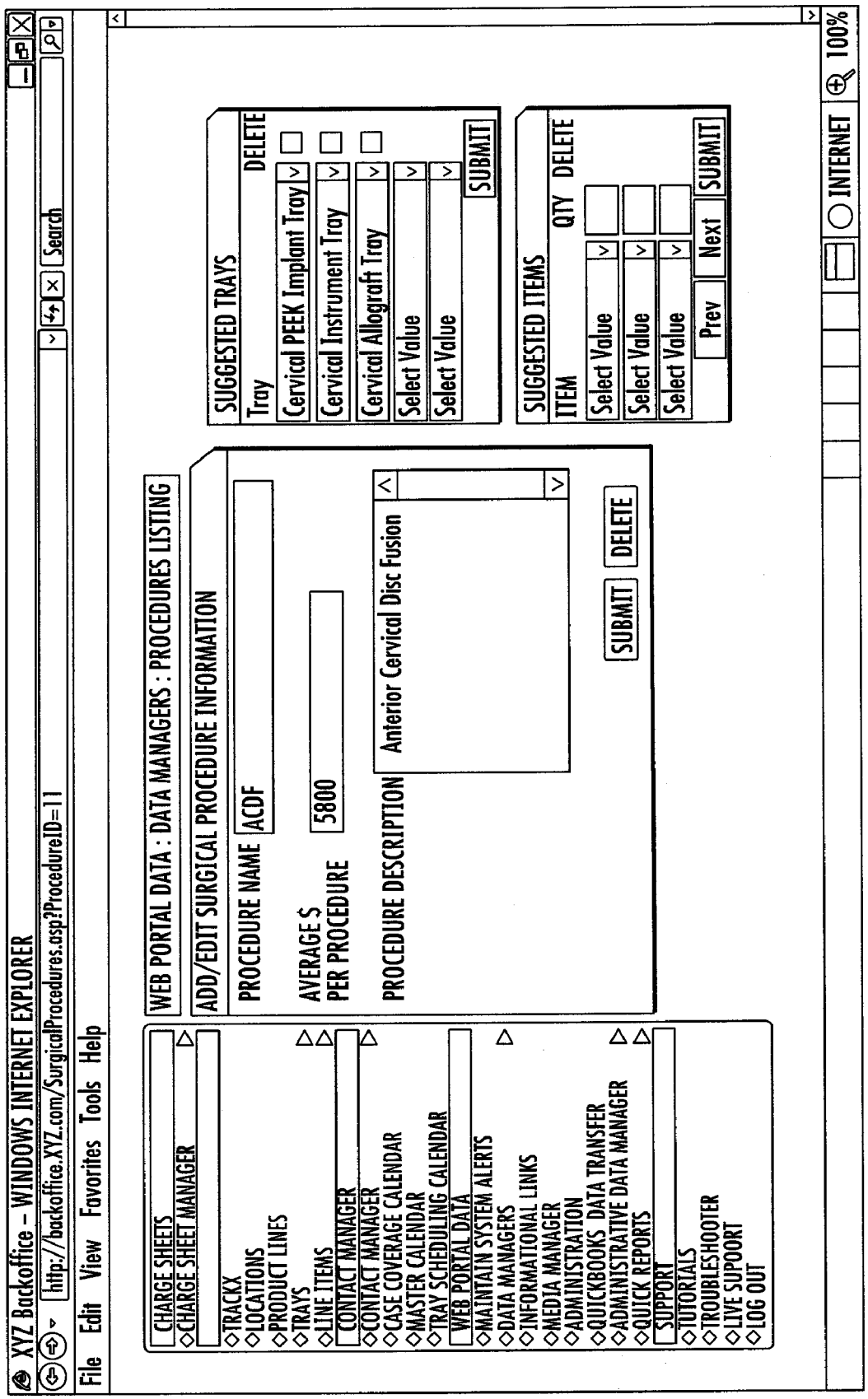
FIG. 9 is a web page for entering surgical procedure information.

The information with respect to different surgical procedures and the medical trays required for the procedures is illustrated in FIG. 9. The rep. can select the various trays which the surgeon will need or has requested for the procedure. This information is submitted to the system to indicate the availability of the trays and if certain trays must be supplied from other locations. If this is the case then an order is placed and the required tray is shipped to the desired location.

Figure 10:
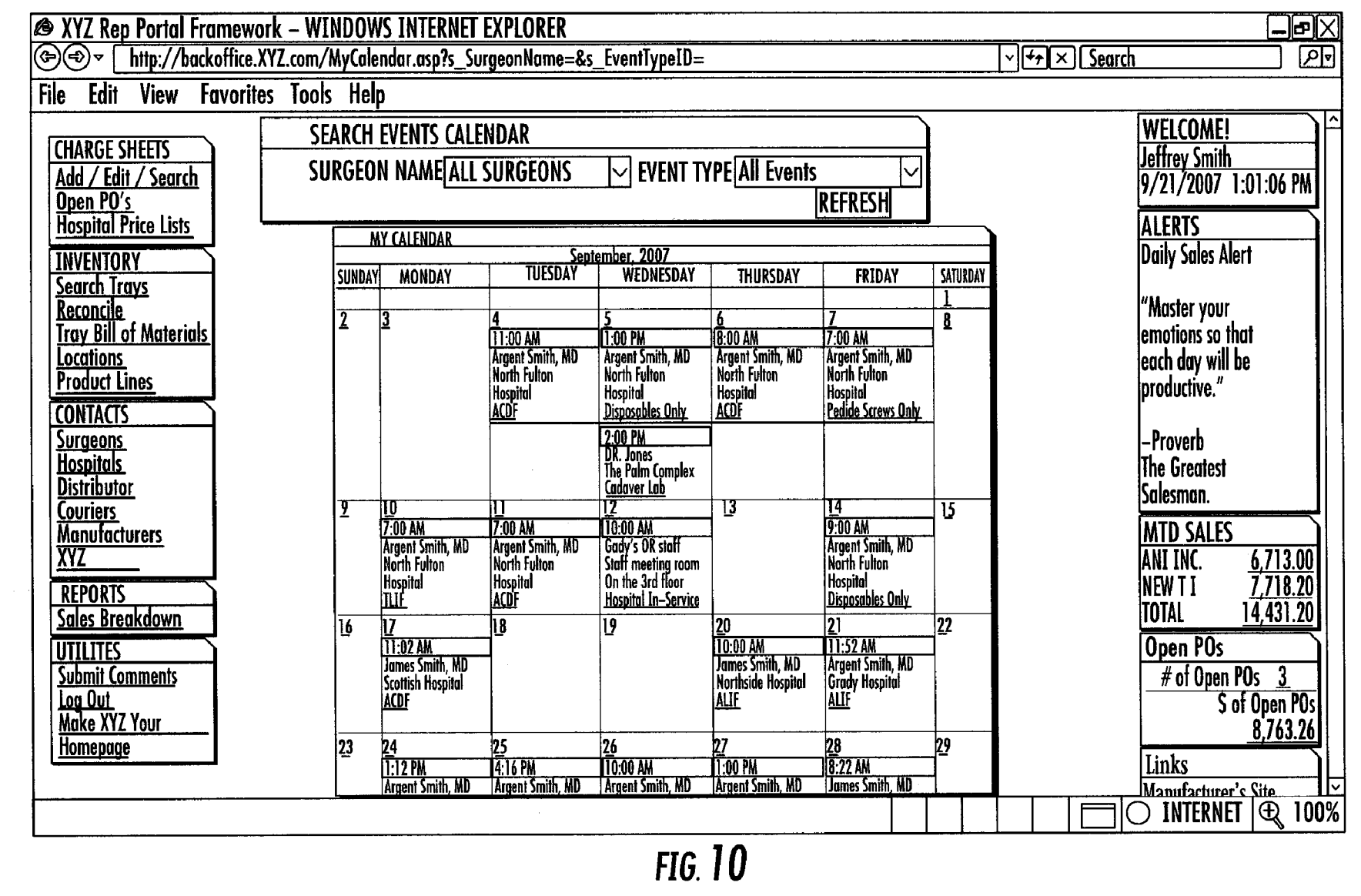
Figure 11:
FIG. 11 is a web page illustrating surgeons information.

FIG. 10 illustrates a medical rep's calendar. His surgeries and other activities are on the calendar. He can also access he sales information, track the medical inventory and access information with respect to his contacts. All of this can be done where ever he has access to the Internet. An example of the information regarding specific surgeons is illustrated in FIG. 11. With this information he is better equipped to establish a working relationship with the surgeon. Should the rep. need information regarding specific tray, he can also access this as illustrated in FIG. 12. This information includes an identification of the trays, the location of the trays, information regarding a hospital at which the tray is required, the date on which the tray is to arrive at the hospital, the date of the surgery and the date the tray will be available again if it is not needed for the surgery.

Figure 13:
FIG. 13 is a web page illustrating inventory orders for medical trays.
Figure 14:
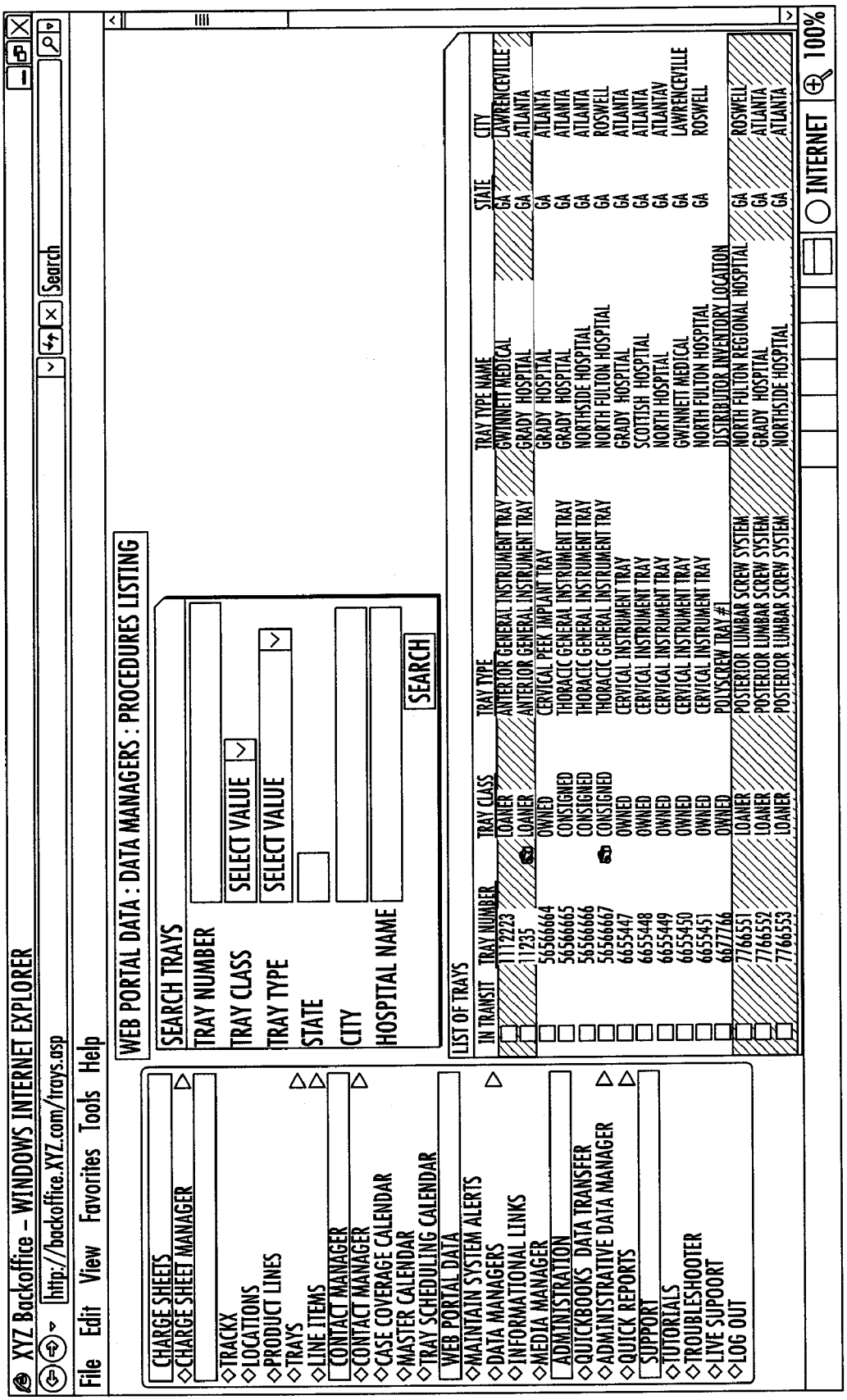
FIG. 14 is a web page illustrating the location of medical trays.

An inventory of tray orders is illustrated in FIG. 13. The date of the surgery, the surgeon's name, the specific tray required, the hospital and the rep's name assigned to the tray are provided. The rep can then locate an appropriate tray and assign it to the surgery. A list of the trays available is illustrated in FIG. 14. This information lists the specific trays, the location of the tray, if the tray has already been purchased by the hospital and any special notes regarding the tray. The notes are indicated by an icon next to the tray class.

Figure 15C:
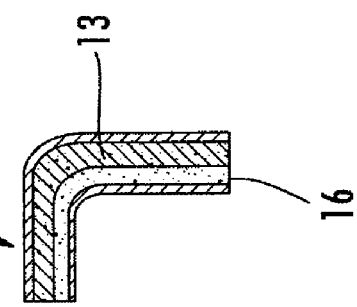
FIG. 15 A-C illustrates an embodiment of a tracking device for a medical tray.
Figure 15B:
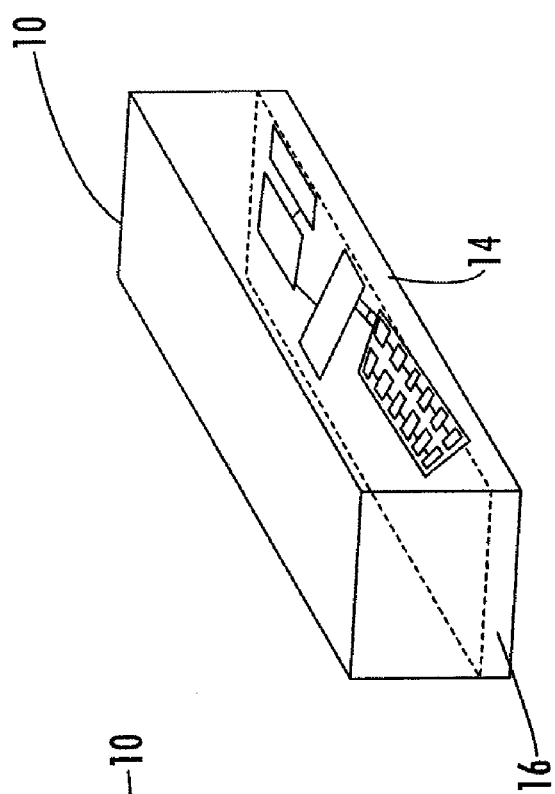
Figure 15A:
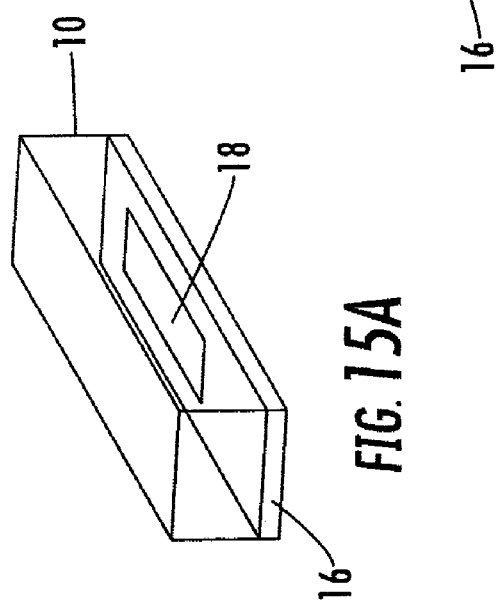
Figure 16A:
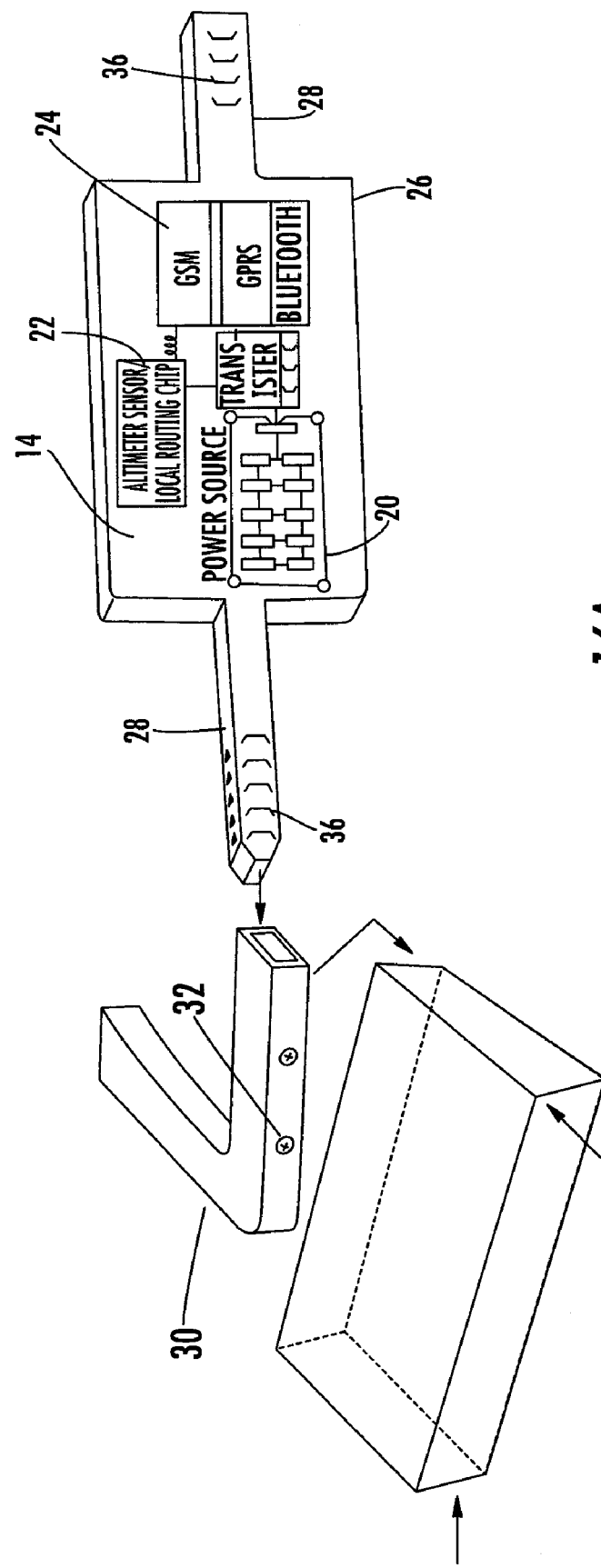
FIG. 16 A-C illustrates another embodiment of a tracking device for a medical tray and FIG. 17 illustrates another embodiment of a tracking device for a medical tray.
Figure 17:
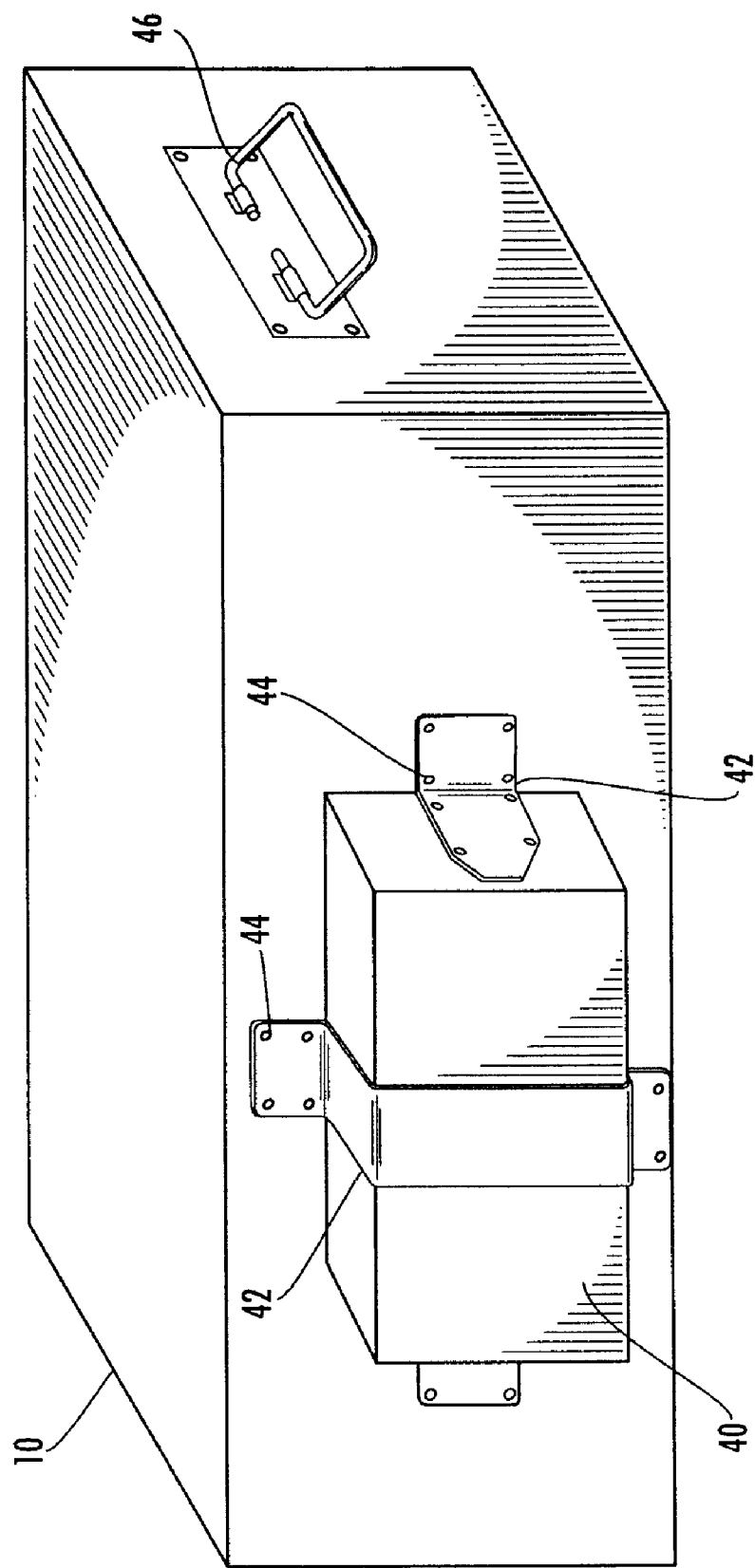

Various tracking devices for the medical trays are illustrated in FIGS. 15-17. In FIGS. 15A and 15B the medical tray of the present invention is indicated as 10. The tray normally comprises a rectangular closed box. The surgical instruments (not shown) are arranged within the tray to insure proper sterilization. The tray is preferably composed of a nylon-like thermo-resistant polymer exterior 12 and has a similar interior. Other materials with the desired properties could also be utilized. The tracking device 12 is located in the lower portion of the tray, FIG. 15B. The tracking device is placed in the lower portion of the tray in a silicone foam material 16. The silicone foam functions as both an insulator and a shock absorption device. The medical trays are normally sterilized at temperatures above 270° F. and the silicone foam helps protect the tracking device from these high temperatures. Once the tracking device is placed in the lower portion of the tray 10 an access door 18 is secured in a manner that prohibits unauthorized personnel from accessing the tracking device. The access door is preferably provided with waterproof and heat resistant seal (not shown). The access door is used for battery replacement in the power source. The foam can be a silicone/polyamide or a silicone/polyimide. The tracking device 14, as illustrated in FIG. 16A, comprises a power source 20, a motion sensor 22, and a communicator or first transceiver 24 which utilizes GSM, GPRS, CDMA, SMS and/or Bluetooth to communicate the location of the medical tray. An individual seeking the location of the medical tray can establish contact with the tracking device with their mobile phone or second transceiver. The tracking device will then indicate the location of the medical tray. This type of communication system permits the tracking of medical trays inside of buildings where GPS devices will not function. The individual's mobile communication device (second transceiver) or another communication device (second transceiver) can be programmed to ping the tracking device at regular intervals. This helps conserve the batteries in the power supply of the tracking device. The motion sensor 22 triggers the communicator or first transceiver 24 when ever the tray is moved.

A second embodiment of the tracking device is illustrated in FIGS. 16 A-C. This tracking device is secured around the outer periphery of the medical tray. This is known as the "Halo" design. The tracking device is located in the main element 26 of the device. The tracking device includes a motion sensor 22, a power supply 20 and a communicator or first transceiver 24. An access door or panel (not shown) provides access to the tracking device to enable battery replacement or other operations. The access door cannot be readily accessed by unauthorized personnel and is normally located on the rear side of the main element 26. The main element 26 is provided with legs or extensions 28. These legs connect to corner elements 30. The legs are secured to the corner elements utilizing rivets or other fasteners 32. A connection member 34 secures corner elements together, as illustrated in FIG. 16C. The corner elements 30 are designed to connect to each other when they are secured to a conventional sized medical tray. Connection members 34 can also be utilized to connect corner elements 30 to each other whenever the width of the medical tray is larger than normal. A connection member 34 is illustrated in FIG. 16B. The connection member 34 is provided with zip-tie like one way connectors 36 at both ends of the connection member. These connectors allow the connection member to be inserted into the corner elements but not withdrawn therefrom. After these elements have been connected to each other, additional fasteners such as rivets 32 are also used to secure the elements together. Connectors 36 are also provided on the main element 26 as illustrated in FIG. 16A. The medical tray is formed from the same material as the tray of the embodiment of FIGS. 15 A-C. Thermo resistant foam can also be utilized in the main element to protect the tracking device.

A third embodiment of the tracking device is illustrated in FIG. 17. The tracking device is positioned in a housing 40 which is secured to an outer portion of a medical tray 10. Straps 42 secure the housing 40 to the medical tray. Rivets 44 or similar fasteners secure the straps 42 to the medical tray. The fasteners are designed so they are not removable by unauthorized personnel. An access door or panel (not shown) provides access to the interior of housing 40 for battery replacement or access to the tracking device. A handle 46 can be provided on the medical tray to assist in transporting the tray. The medical tray is formed from the same material as the tray of the embodiment of FIG. 15 A-C. Thermo resistant foam can also be utilized in the housing 40 to protect the tracking device All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A tracking system comprising:
   a first communicator located in at least one object to be tracked;
   a second communicator receiving signals from said first communicator;
   said first communicator and said second communicator are located proximate each other and being encased in a material which provides thermal protection during an autoclaving process, said first communicator and said second communicator being located in said at least one object to be tracked;
   a third communicator communicating with said first communicator to provide said first communicator with information regarding the identification and the location of said at least one object to be tracked;
   said second communicator transmitting information to a network server with respect to the location of said at least one object to be tracked, said information includes identification of said at least one object to be tracked;
   said tracking system including information regarding the intended use of said at least one object to be tracked; said system enabling a user to arrange delivery of said at least one object to be tracked to a location where said at least one object to be tracked is to be utilized;
   said system further including information regarding the intended user of said at least one object to be tracked;
   said system enabling a user of said system to schedule the use of and arrange the location said at least one object to be tracked so that said intended user will have use of said at least one object to be tracked when necessary.

2. The tracking system of claim 1 wherein said information regarding the identification and location of said at least one object to be tracked and said information regarding the intended use and intended user of said at least one object to be tracked is transmitted to a cellular network tower using CDMA and processed through a back end server which information is later contained in the web-based platform.

3. The tracking system of claim 1 wherein said information regarding the identification and location of said at least one object to be tracked and said information regarding the intended use and intended user of said at least one object to be tracked is transmitted to a global satellite using GPS, AGPS and GPRS and processed through a back end server which information is later contained in the web-based platform.

4. The system of claim 1 wherein information regarding the intended user of said object is retained in said system.

5. The system of claim 1 wherein information regarding the user of said system is retained in said system.

6. The system of claim 1 wherein information regarding the location of said at least one object and other intended locations of said at least one object is retained in said system.

7. The system of claim 1, wherein said object is a medical device.

8. The system of claim 4 wherein said intended user is a doctor.

9. The system of claim 1 wherein said object is a medication.

10. The system of claim 1 wherein said object is a patient.

11. The system of claim 1 wherein said user is a representative of a medical device manufacturer.

12. The system of claim 11 wherein said representative can order specific medical devices.

13. An independent mobile tracking device for an object comprising;
    a first communicator located proximate at least one object to be tracked;
    a second communicator receiving signals from said first communicator;
    said first communicator and said second communicator are located proximate each other and being encased in a material which provides thermal protection during an autoclaving process, said first communicator and said second communicator being located in said at least one object to be tracked;
    a third communicator communicating with said first communicator to provide said first communicator with information regarding the location of said at least one object to be tracked;
    said second communicator transmitting to a network server said information regarding the location of said at least one object to be tracked, said information regarding the location of said at least one object includes identification of said at least one object and a device to activate said second communicator.

14. The tracking device of claim 13 wherein said information regarding the location of said at least one object is transmitted to a mobile phone using CDMA.

15. The tracking device of claim 13 wherein said object is a medical tray and said first communicator is located in said medical tray.

16. The system of claim 1 wherein signals are transmitted to a cellular network tower using GSM and processed through a back end server which information is later contained in a web-based platform.

17. The system of claim 1 wherein signals are transmitted to a cellular network tower using CDMA and processed through a back end server which information is later contained in software.

18. The system of claim 1 wherein signals are transmitted to a cellular network tower using GSM and processed through a back end server which information is later contained in a web-based platform and software.

19. The system of claim 1 wherein signals are transmitted to a cellular network tower using CDMA and processed through a back end server which information is later contained in a web-based platform and software.

20. The system of claim 1 wherein signals are transmitted to a cellular network tower using GSM and processed through a back end server which information is later contained in a web-based platform and software.

21. The system of claim 1 wherein said information regarding the identification and location of said at least one object to be tracked and said information including the identification of said at least one object to be tracked is transmitted to a cellular network tower using AGPS and processed through a back end server which information is later contained in a web-based platform and software.

22. The system of claim 1 wherein signals are transmitted to a global satellite using GPS, AGPS and GPRS and processed through a back end server which information is later contained in the software.

23. The system of claim 1 wherein signals are transmitted to a global satellite using GPS and processed through a back end server which information is later contained in a web-based platform.

24. The system of claim 1 wherein signals are transmitted to a global satellite using GPS and processed through a back end server which information is later contained in software.

25. The system of claim 1 wherein signals are transmitted from a global satellite and combined with information from a network using AGPS and processed through a back end server which information is later contained in a web-based platform.

26. The system of claim 1 wherein signals are transmitted from a global satellite and combined with information from a network using AGPS and processed through a back end server which information is later contained in software.

27. The system of claim 1 wherein signals are transmitted from a global satellite and combined with information from a network using AGPS and processed through a back end server which information is later contained in a web-based platform and software.

28. The system of claim 1 wherein signals are transmitted through a communication network using GPRS and processed through a back end server which information is later contained in a web-based platform.

29. The system of claim 1 wherein signals are transmitted through a communication network using GPRS and processed through a back end server which information is later contained in software.

30. The system of claim 7 wherein said medical device is a steam sterilizable implant.

31. The system of claim 7 wherein said medical device is a steam sterilizable instrument.

32. The system of claim 7 wherein said medical device is a steam sterilizable battery for operation of an instrument.

33. The system of claim 7 wherein said medical device is a steam sterilizable container.

34. The tracking device of claim 13 wherein said at least one object to be tracked is a medical tray and said communicator is located on said medical tray.

35. The tracking device of claim 13 wherein said at least one object to be tracked is a medical tray and said first and said second communicators are attached to said medical tray.

36. The system of claim 7 wherein said medical device is an autoclavable implant.

37. The system of claim 7 wherein said medical device is an autoclavable instrument.

38. The system of claim 7 wherein said medical device is an autoclavable battery for operation of an instrument.

39. The system of claim 7 wherein said medical device is an autoclavable container.

40. The system of claim 7 wherein said medical device is a dry heat sterilizable implant.

41. The system of claim 7 wherein said medical device is a dry heat sterilizable instrument.

42. The system of claim 7 wherein said medical device is a dry heat sterilizable battery for operation of an instrument.

43. The system of claim 7 wherein said medical device is a dry heat sterilizable container.

44. The system of claim 1 wherein said first communicator is a Bluetooth device.

45. The system of claim 1 wherein said second communicator is a SMS enabled device.

46. The tracking device of claim 13 wherein said first and said second communicators are located in a lowermost portion of a medical tray.

47. The tracking device of claim 13 wherein said first communicator is a Bluetooth device and said first and said second communicators are located in a lowermost portion of a medical tray.

48. The tracking device of claim 13 wherein said second communicator is a SMS enabled device and said first and said second communicators are located in a lowermost potion of said medical tray.

49. The system of claim 7 wherein said medical device is a non-sterile container for medical parts.

50. The system of claim 7 wherein said medical device is a computer system.

51. The system of claim 1 wherein said first communicator is a radio frequency identification (RFID) reader.

52. The system of claim 1 wherein said third communicator is a radio frequency identification (RFID) tag.

53. The system of claim 1 wherein said third communicator is a Bluetooth chip.

54. The system of claim 1 including a motion sensor, said motion sensor located in said at least one object to be tracked, said motion sensor communicating with said second communicator.

55. The system of claim 1 wherein said second communicator includes a pager.

56. The system of claim 1 wherein said second communicator includes a beeper.

57. The tracking device of claim 13 wherein said information regarding the location of said at least one object to be tracked is transmitted to a mobile phone using GSM.

58. The tracking device of claim 13 wherein said information regarding the location of said at least one object to be tracked is transmitted to a mobile phone using SMS.

59. The tracking system of claim 1 wherein said information regarding the identification and location of said at least one object to be tracked and said information regarding the intended use and intended user of said at least one object to be tracked is transmitted to a cellular network tower using CDMA and processed through a back end server which information is later contained in software.

* * * * *